United States Patent [19]
Wallace et al.

[11] Patent Number: 5,522,864
[45] Date of Patent: Jun. 4, 1996

[54] APPARATUS AND METHOD FOR OCULAR TREATMENT

[76] Inventors: Larry B. Wallace, 1139 Ellis Hollow Rd., Ithaca, N.Y. 14850; Kevin A. Digney, 7130 Woodchuck Hill Rd., Fayetteville, N.Y. 13066

[21] Appl. No.: 329,094

[22] Filed: Oct. 25, 1994

[51] Int. Cl.$^6$ .................................................. A61N 1/20
[52] U.S. Cl. ............................... 607/53; 607/44; 607/75; 607/141
[58] Field of Search ............................... 607/244, 53, 54, 607/115, 139, 141, 145, 149, 150, 151, 75; 600/26

[56] References Cited

U.S. PATENT DOCUMENTS

| | | |
|---|---|---|
| 793,004 | 6/1905 | May . |
| 1,684,840 | 9/1928 | Catlin ........................................ 607/141 |
| 4,018,218 | 4/1977 | Carlson et al. ........................ 607/070 X |
| 4,326,529 | 4/1982 | Doss et al. . |
| 4,603,697 | 8/1986 | Kamerling . |
| 4,614,193 | 9/1986 | Liss et al. . |
| 5,025,811 | 6/1991 | Dobrogowski et al. . |
| 5,099,829 | 3/1992 | Wu . |
| 5,147,284 | 9/1992 | Fedorov et al. . |
| 5,174,304 | 12/1992 | Latina et al. . |

*Primary Examiner*—William E. Kamm
*Assistant Examiner*—Jeffrey R. Jastrzab
*Attorney, Agent, or Firm*—Harris Beach & Wilcox

[57] ABSTRACT

Macular degeneration and other ocular pathology in a subject is treated by the steps of: placing a positive electrode of a direct current source in electrical contact with a closed eyelid of a subject; placing a negative electrode of the source in electrical contact with the posterior neck of the subject; and causing a constant direct current of 200 µA to flow between the electrodes through the subject for about 10 minutes. The source can be a portable, battery powered constant direct current generator which is affixed to the subject. The subject is thus enabled to ambulate during treatment.

23 Claims, 5 Drawing Sheets

5,522,864

APPARATUS AND METHOD FOR OCULAR TREATMENT

BACKGROUND OF THE INVENTION

1. Field of the Invention

This invention relates to the medical treatment of ocular disease. More particularly this invention relates to an electronic apparatus for the application of electrical current to the eye for treating diseases thereof, for example macular degeneration.

2. Description of the Prior Art

Macular degeneration is a debilitating ocular disease having hemorrhagic and exudative variants, both of which are susceptible to safe and efficient treatment by the invention hereof. Treatment typically results in amelioration of the ophthalmoscopic manifestations of the disorder, and substantial restoration of central visual acuity.

It is proposed in Fedorov et al., U.S. Pat. No. 5,147,284, to treat diseases of the optic nerve and retina by the application of a pulsed 3.5 magnetic flux, the magnetic field induction being from 0.1 T to 0.25 T. However the technique is invasive, requiring exposure of the posterior portion of the eyeball and optic nerve and introduction of the inducer into the orbit.

It is proposed to treat glaucoma with the application of transcutaneous electrical stimulation from Liss et al., U.S. Pat. No. 4,614,193. Liss et al. discloses the application of pulsed electrical current at a level less than 4 milliamperes, the pulse trains occurring at 12–20 kHz, amplitude modulated at 8–20 hz, and having a 3:1 duty cycle. Applying this waveform through electrodes positioned on the temple and on the ipsilateral hand, Liss et al. achieved an approximately 28% reduction in intraocular pressure in the treated eye. To the knowledge of the inventors, passage of electrical current through the eye (hereinafter "transocular electrical conduction") has not been used in the art for the treatment of macular degeneration.

SUMMARY OF THE INVENTION

It is therefore a primary object of the present invention to provide an improved apparatus and method for the treatment of macular degeneration and certain other ocular pathology.

It is another object of the present invention to provide a safe, improved, noninvasive method for the restoration of vision by treating the eye with transocular conduction of electrical current.

These and other objects of the present invention are attained by a direct current generator that produces low level direct current, electrodes being placed on the closed eyelid and on or near the occiput of the skull. The inventors have found that this waveform is particularly effective in the treatment of macular degeneration, and is believed to benefit a variety of other ocular disorders. While the principles under which the invention produces its beneficial effects are not fully understood, and without restriction to a particular theory of operation, it is suggested that transocular electrical conduction as practiced in accordance with the invention may restore cellular electrical balance by changing potentials across cell membranes. This may alter the levels of certain ions and molecules toward a desirable equilibrium. Other physiological effects are believed to be produced: reduction of alkalinity proximate the passage of electrical current and the production of low levels of hydrochloric acid; attraction of oxygen to the region; localized vasoconstriction; reduction of local hemorrhage; sedation; increased tonicity of local tissues; antisepsis; production of desirable fibroplasia; and reduced neuromuscular irritability.

In accordance with one aspect of the invention macular degeneration in a subject is treated by the steps of: placing a first electrode of a direct current source in electrical contact with a closed eyelid of a subject; placing a second electrode of the source in electrical contact with a site remote from the eyelid of the subject; and causing a direct current of 1–1000 µA to flow between the electrodes through the subject for about 10 minutes.

In accordance with another aspect of the invention the source is a portable, battery powered constant direct current generator which is affixed to the subject. The subject is thus enabled to ambulate while the direct current is flowing therethrough.

In accordance with yet another aspect of the invention, the first electrode is a positive electrode, and the second electrode is a negative electrode. The remote site for the second electrode is the posterior neck of the subject.

In accordance with still another aspect of the invention, the current flowing between the electrodes is 200 µA, and is constant in magnitude.

BRIEF DESCRIPTION OF THE DRAWING

For a better understanding of these and other objects of the present invention, reference is made to the detailed description of the invention which is to be read in conjunction with the following drawings, wherein.

DESCRIPTION OF THE PREFERRED EMBODIMENT

Figure 1:
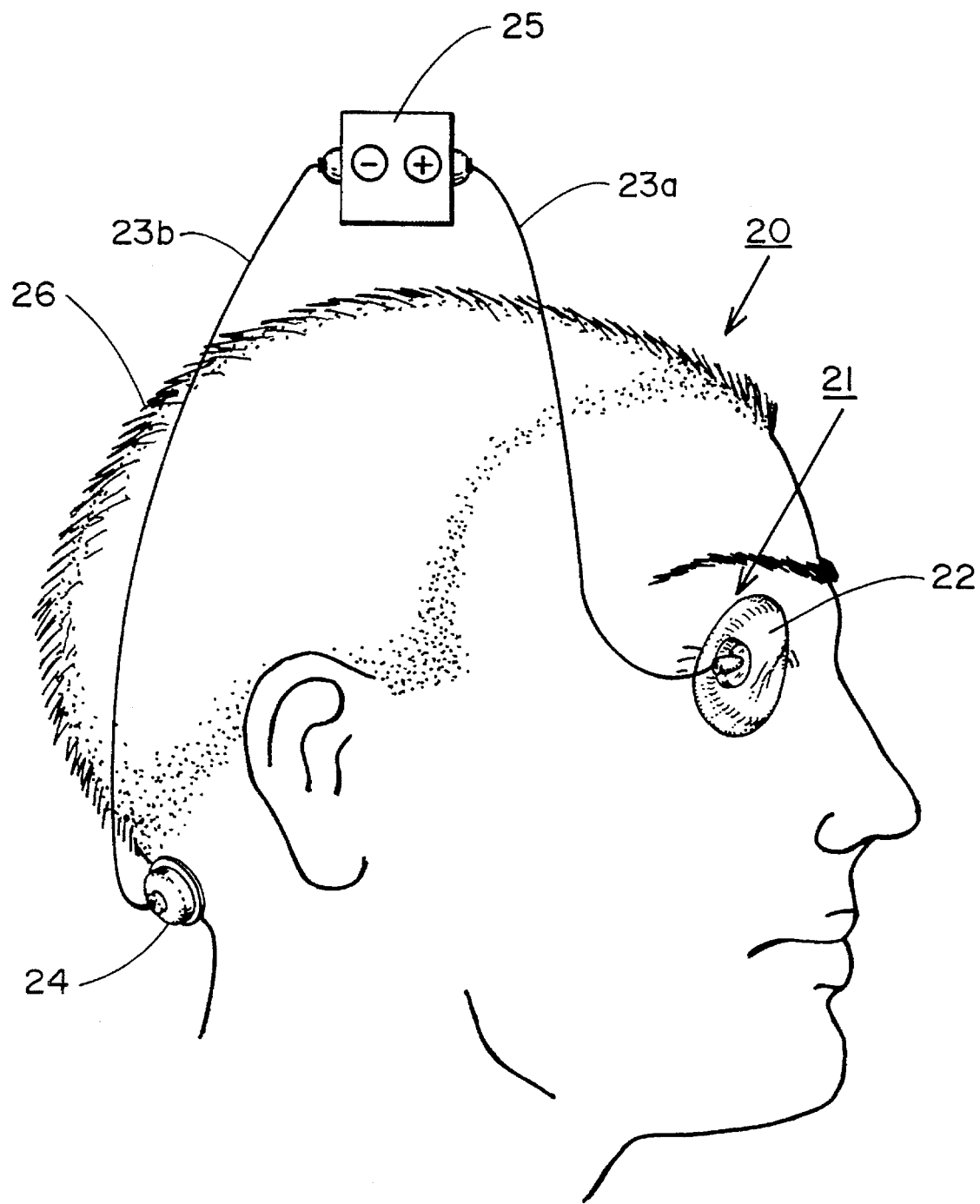
FIG. 1 is a side view of a subject receiving current to the eye that is delivered in accordance with a first embodiment of the invention.
Figure 2:
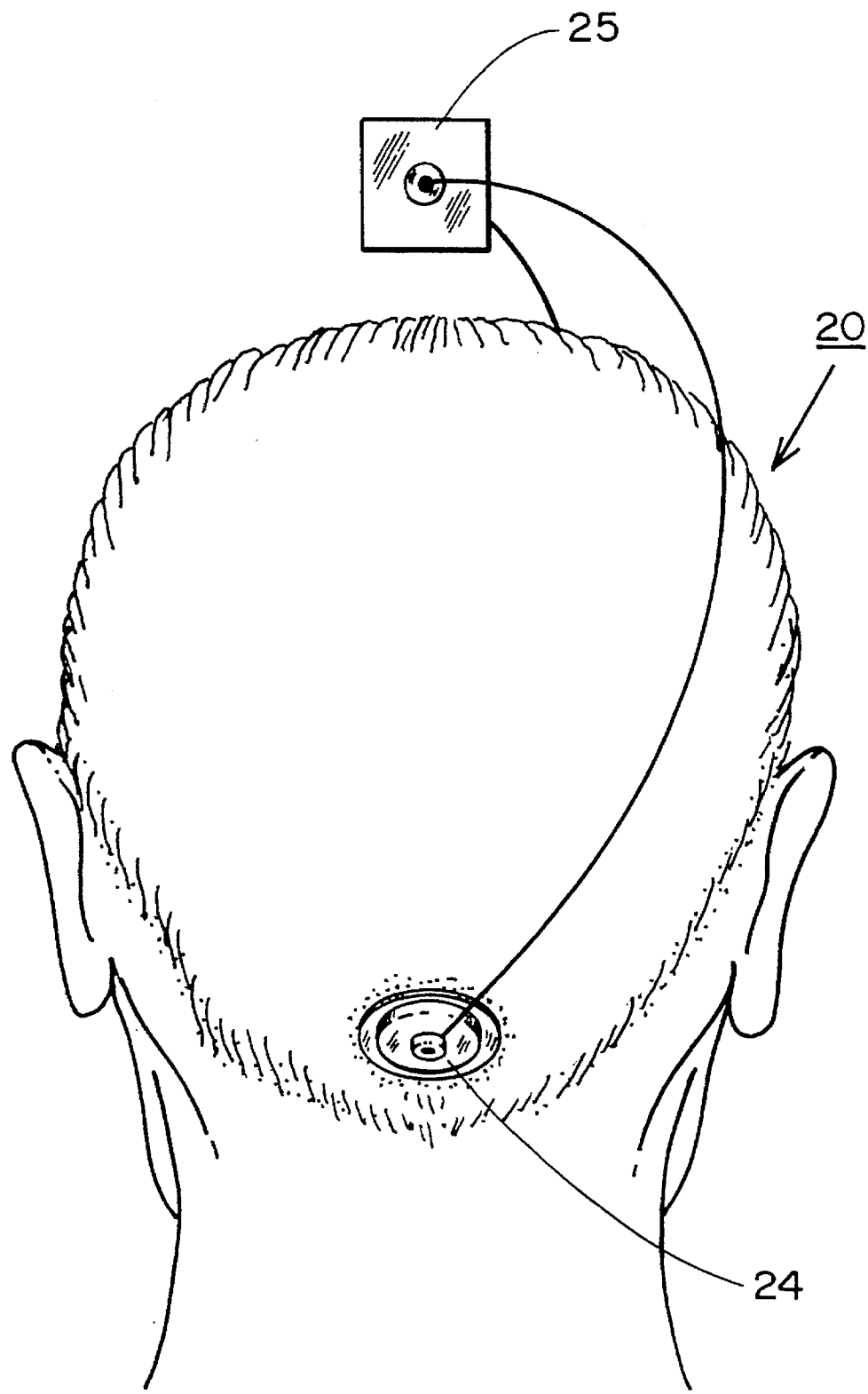
FIG. 2 is a rear view of the subject shown in FIG. 1.

Turning now to the Drawing and to FIGS. 1 and 2 thereof, there is shown a subject 20 having the closed lids of an eye 21 in contact with a sponge electrode 22. The sponge electrode 22 is connected to the positive output of a constant current generator 25 having a suitable power source (not shown) connected thereto or incorporated therein. The negative output of the generator 25 is connected to an occipital electrode 24, which is attached to the skin at the occiput, substantially in the midline. When the generator 25 is activated, a current loop is established that extends in order from the generator 25 through the sponge electrode 22, the eye 21, the cranium 26, and the second electrode 24. The loop is completed at the generator 25.

Figure 4:
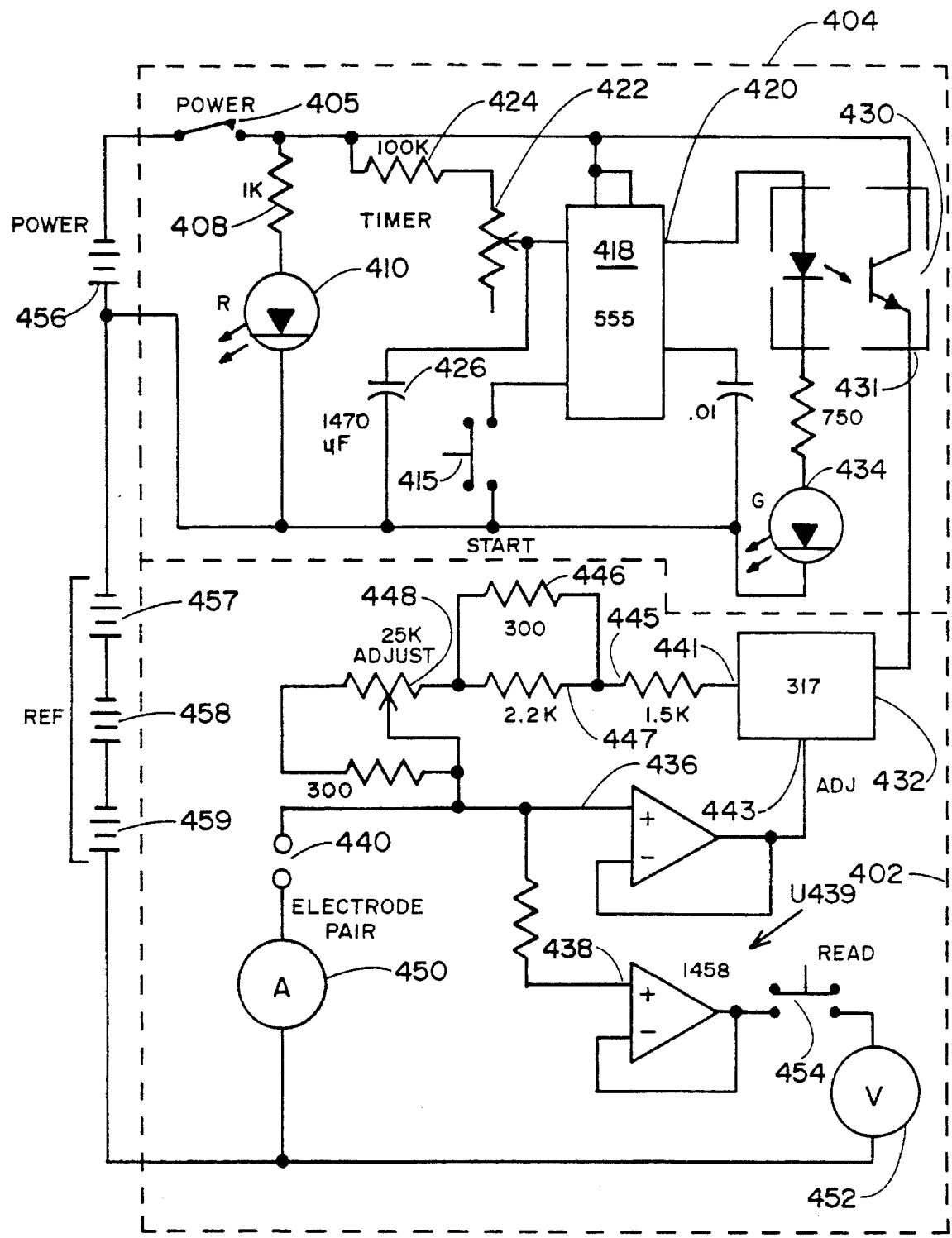
FIG. 4 is a schematic of a constant current source suitable for delivering current to the eye in accordance with the invention.

In FIG. 4 there is shown an electronic circuit of a constant current source that is included in a preferred embodiment of the invention. The circuit is designed to deliver a constant current of between 5 µA and 1 mA to the eye for the treatment of ocular diseases, such as macular degeneration. A current delivery of 200 µA is preferred. The unit is composed of two blocks, a current source 402 and a timer 404. It operates as follows:

Upon closure of switch 405, power is applied to the circuit. Resistor 408 and LED 410 act as an indicator light for the power-on condition. Switch 415 acts as a trigger for the timer. When this button is pressed, a voltage is applied to pin 420 of integrated circuit 418 for a period of time determined by the setting on potentiometer 422 and the values of resistor 424 and capacitor 426. This causes a voltage to be passed through the optical isolator 430, which in turn causes a voltage to be applied to pin 431 of the optical isolator 430. LED 434 indicates that switch 415 has been depressed, and that treatment has been initiated. Voltage regulator 432, which is preferably of type LM317, is such that it maintains a constant voltage of 1.25 volts across its output pin 441 and adjust pin 443. From Ohms law then, since pins 436 and 439 of U439 see a very high impedance, the current through the electrodes 440 is 1.25/R Amperes, where R is the net resistance across the output and adjust pins 441, 443 of the voltage regulator 432 as determined by the resistance of the network of resistors 445–447 and trimmer potentiometer 448. The magnitude of the current is set by adjustment of the trimmer potentiometer 448. The current through the electrodes is independent of the resistance thereacross within an operating range, and is monitored by the ammeter 450. Switch 454 allows the operator to read the voltage across the electrodes. Battery 456 supplies power to operate the timer circuit 404. Batteries 457–459 are included to provide a larger voltage reference across the electrodes so that the constant current can be maintained over a larger range of electrode resistance.

Figure 5:
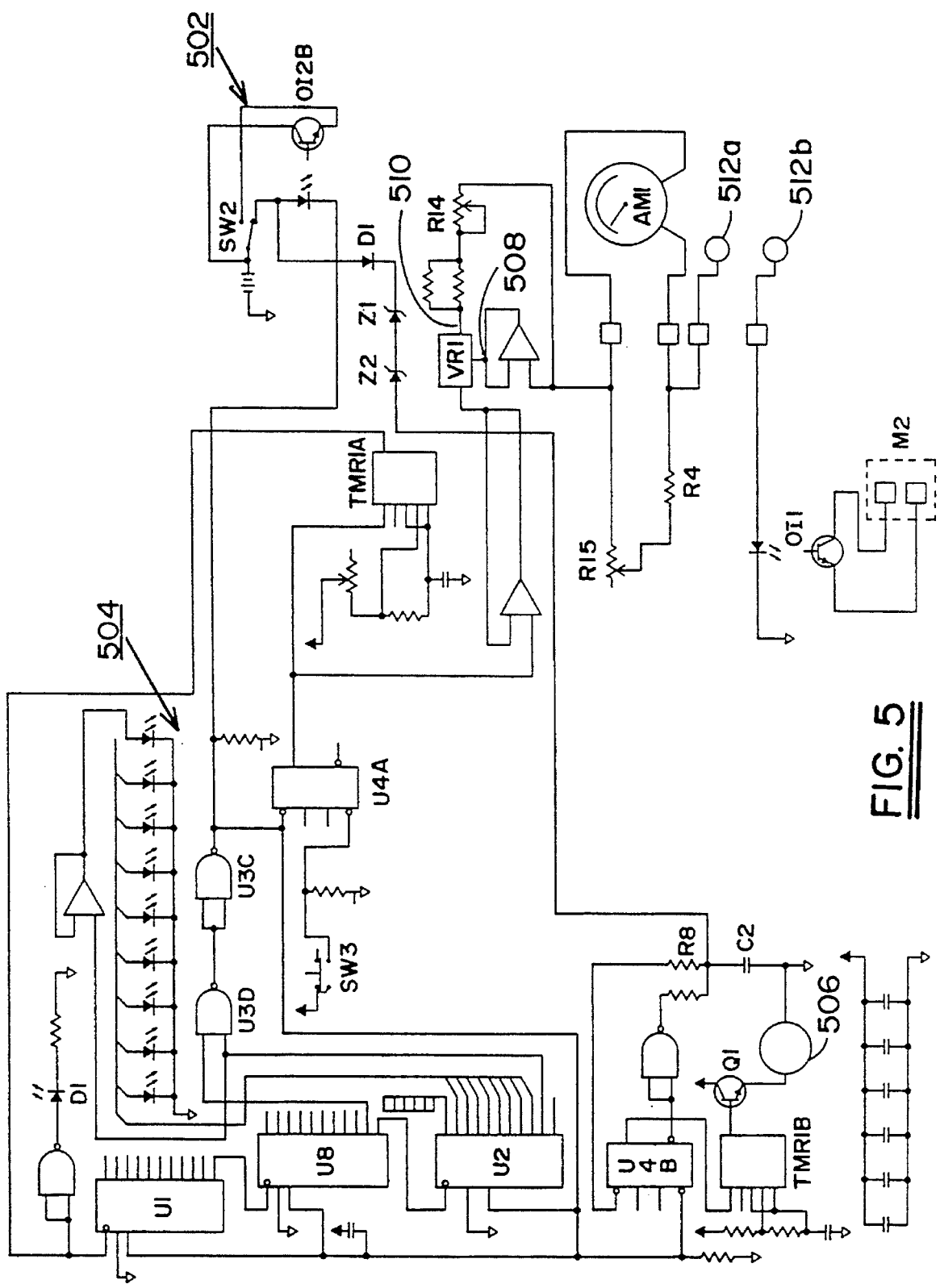
FIG. 5 is a schematic of another constant current source designed to deliver a current through the eye in accordance with the invention.

The constant current source can also be realized as explained with reference to FIG. 5. This shown a schematic of another constant current source designed to deliver a 5–1000 μA current through the eye. The major circuit components consist of a current source and a timer. When momentary switch SW2 is turned on, a small current flowing through LED Ol2A in the optoisolator 502 turns on the SCR Ol2B which powers VCC throughout the circuit. Holding the switch SW2 in an on position also causes the reset net of the circuit to become activated. Turning the switch SW2 to the off position (also momentary) switches the battery voltage to the gate of the SCR Ol2B, thereby shutting it down. A tone will be emitted from the unit whenever the switch is held in either position. D2, Z1 and Z2 form a circuit which will cause a continuation of the audio tone for approximately one second upon startup of the unit in the event of a low battery.

Pressing the start-treatment push-button SW3 activates flipflop U4A, which turns on the constant current source, and turns on the reset line to timer TMR1A, starting the clock. As the clock pulses, LED D1 will flash. The clock pulses are counted by U1, U8, and U2, and every one hundred counts of the clock causes a shift in the light bar 504, U3C and U3D combine to reset flipflop U4A when the count reaches 100% of the treatment time. This causes the constant current source to turn off, the counters to reset, and flipflop U4B to set. This flipflop turns on timer TMR1B, which in turns causes transistor Q1 to conduct. This causes the audio alarm 506 to sound for about one second. U3B charges C2 through R8 until U4B resets. At this point the circuit is back to its original ready state, where it remains until the start-treatment push-button SW3 is pushed, or the unit is switched off.

The constant current source VR1 is preferably an LM317 variable voltage regulator, which by its design maintains a constant voltage between its output pin 508 and its adjust pin 510 of 1.25 volts. This constant voltage across a fixed resistance causes a constant current to be delivered through the electrodes to ground when the impedance of the entire path is low enough to allow that much current, given that the circuit has a 9 V voltage limitation. R14 allows the resistance to be adjusted in order to vary the magnitude of the treatment current.

AM1 is a 100 μA DC ammeter. R4 and potentiometer R15 provide an adjustable shunt so that the meter can be adjusted to read correctly for any selected treatment current.

Ol1 is an optical isolator which is connected to a self powered elapsed time meter M2. This meter will only log time when current is passing through the electrode jacks 512a, 512b regardless of the state of the unit. For example, if the unit is on, but the electrodes are not connected to a patient, time will not be logged until the electrodes are connected to the patient, or are otherwise placed in electrical connection.

Use of the invention will now be explained with reference to FIGS. 1 and 2. The patient 20 has an ocular disease such as macular degeneration in the eye to be treated. It is believed that beneficial results are obtained in other ocular disorders. Analgesic medication should be discontinued at least 4–8 hours prior to treatment, so that the patient's ability to perceive pain is not impaired. A constant current generator 25, which can be realized as either the embodiment of FIG. 4, or of FIG. 5, is connected to a patient 20. The positive and negative terminals are connected by two wires 23a, 23b to sponge electrode 22 and occipital electrode 24 respectively, and the constant current generator 25 is connected to a suitable source of power (not shown). The sponge electrode 22 is placed on the closed eyelid, and the occipital electrode 24 placed at the back of the neck substantially in the midline. The contacts are held in place by straps (not shown), which can be fastened by VELCRO (a trademark). The straps are tight enough to prevent the eye from opening during the treatment.

The patient 12 is requested to relax, and the unit then actuated to begin treatment, which is preferably maintained for 10 minutes, after which time the internal timer in the constant current generator 25 shuts down the unit. The straps and contacts are then removed from the patient.

During treatment the patient 20 is preferably monitored for hypotension. It has been found that many patients experience a modest decline in blood pressure during treatment, and it is believed that certain hypertensive patients could benefit from the treatment described.

Treatment is repeated three times per week for at least twelve weeks.

Figure 3:
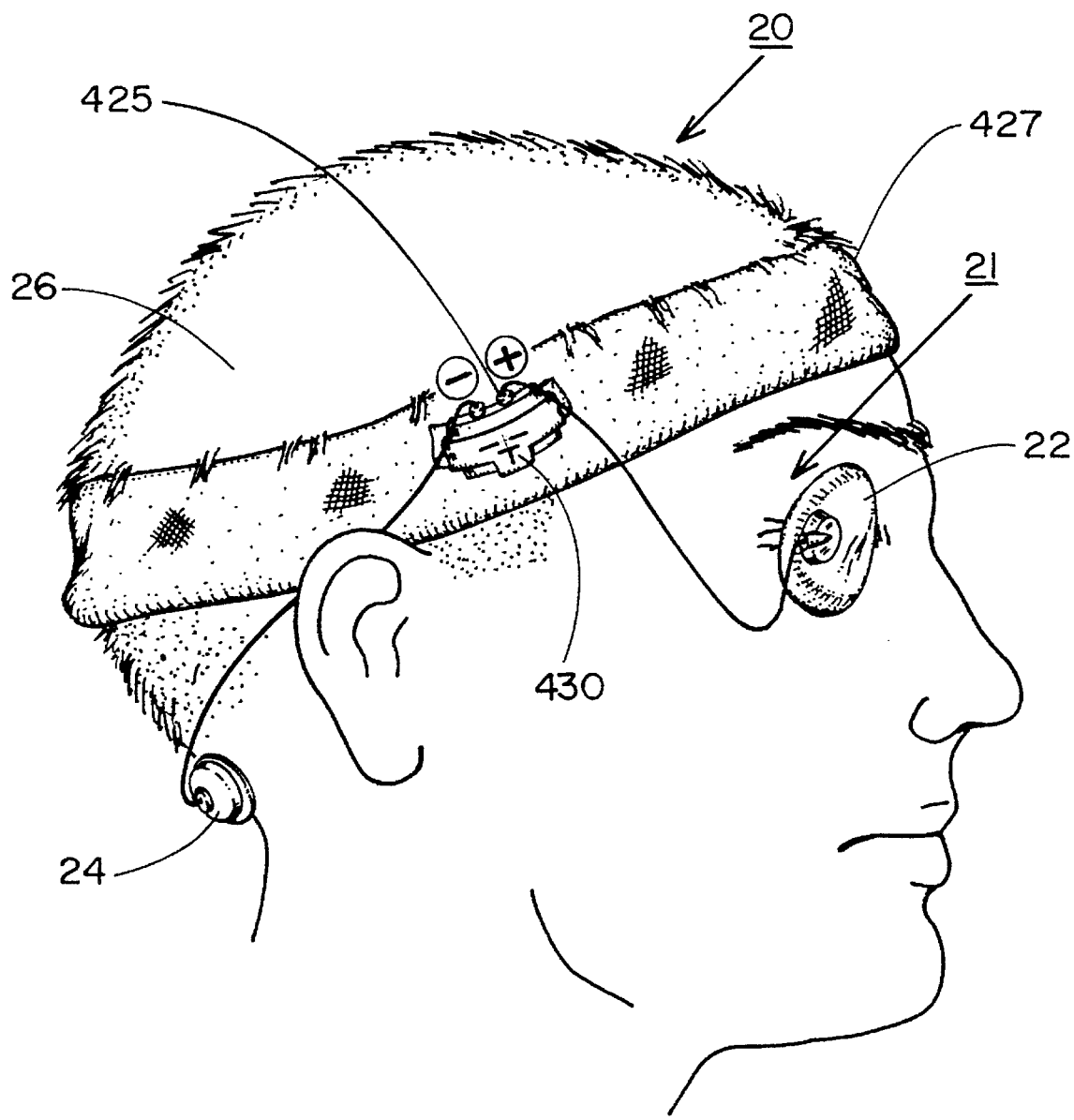
FIG. 3 is a partially schematic side view of a subject receiving current to the eye that is delivered in accordance with a second embodiment of the invention.

Turning now to FIG. 3, there is shown an alternate embodiment of the system. A constant current generator 425, which can be either embodiment described with reference to FIGS. 4 and 5, is constructed in suitable miniature dimensions to be attached to a headband 427. The generator 425 is preferably powered by miniature batteries (not shown). This embodiment is suitable for portable, or home use by patient 20 having macular degeneration, and could also be used for controlling hypertension in certain patients. The generator is connected to the patient 20 in the same manner as described with reference to FIGS. 1 and 2. The patient 20 initiates treatment by depressing momentary switch 430. Treatment then proceeds as described above.

EXAMPLE 1

Patient MH, born Feb. 18, 1916, complained of reduced central visual acuity, and had a medical diagnosis of macular degeneration. She was receiving medication for hypertension and for elevated cholesterol. Prior to treatment the eyes were free of all other pathology. Pupillary responses were normal, and the best corrected visual acuity using the Snellen chart was O.D. 20/200 , O.S. 20/200. Near visual acuity was best corrected to 2M print. Low vision aids were prescribed to assist her adaptation to her visual loss. She returned after 13 months with little change noted on her part. Visual acuity was again measured at the same level, 20/200 in each eye. A contrast sensitivity test was done at the same time, and revealed that visual acuity was in the 20/200 range in both eyes. A visual field examination was normal for both form and blind spot.

One month later she began a series of transocular electrical conduction treatments. Using a constant direct current generator, 200 µA was applied for 10 minutes, with the positive pole attached to the closed eyelid, and the negative pole attached to the back of the neck. After thirteen sessions, averaging three times a week, acuity was remeasured with results as shown in table 1-1.

TABLE 1-1

|  | after 13 sessions | | |
|---|---|---|---|
|  | Right Eye | Left Eye | Both eyes |
| Snellen Chart | 20/100 plus 2 | 20/100 | 20/80 plus 2 |
| Contrast sensitivity | 20/70 | 20/70 | |

At near, the patient could read 1M print easily. The results after 20 sessions are given in table 1-2.

TABLE 1-2

|  | after 20 sessions | | |
|---|---|---|---|
|  | Right Eye | Left Eye | Both eyes |
| Snellen Chart | 20/80 minus 1 | 20/80 minus 1 | 20/70 |
| Contrast sensitivity | 20/70 | 20/80 | |

Treatment was discontinued. A progress evaluation was done two months later with the result as shown in table 1-3

TABLE 1-3

|  | Right Eye | Left Eye | Both eyes |
|---|---|---|---|
| Snellen Chart | 20/80 | 20/80 minus 1 | 20/60 |

Near vision acuity was now 0.8M. The same findings were again duplicated using contrast sensitivity testing.

EXAMPLE 2

Patient JC was born Dec. 15, 1917, and when first seen for evaluation complained of inability to read and see clearly both at far and at near. A diagnosis of macular degeneration was confirmed by two ophthalmologists. He was currently taking medication for hypertension and diabetes. His best corrected visual acuity was OD 20/50; OS 20/30. The eyes were free of all other pathology.

He was treated in the manner described in Example 1. After six treatments, he was re-evaluated with the results shown in table 2-1.

TABLE 2-1

|  | Right Eye | Left Eye |
|---|---|---|
| Snellen Chart | 20/40 | 20/25 |

Blood pressure before and after treatment was 190/80 and 120/70 respectively. Contrast sensitivity done prior to treatment was as follows:

TABLE 2-2

|  | OD | OS |
|---|---|---|
| Aug. 31 | 20/70 | 20/50 |
| Sept 18 | 20/40 | 20/30 |

A visual field examination on September 18 revealed a marked constriction of the color field at near, measured with a one millimeter target at 14 inches. There was also a three time enlargement of the blind spot on the right eye and about a four fold enlargement of the blind spot in the left eye. The color fields were also markedly constricted in the left eye.

Treatment was continued for another eight sessions. He was seen for a progress evaluation on October 5, with the results as shown in Table 2-3.

TABLE 2-3

|  | Right Eye | Left Eye |
|---|---|---|
| Snellen Chart | 20/30 | 20/25 plus 2 |
| Contrast sensitivity | 20/30 | 20/25 |

A visual field was repeated, and there was a marked improvement or expansion in the color fields for both eyes. The blind spot had also reduced and become much more normalized in the right eye, and although enlarged in the left eye, was reduced by 100% over the findings since September 18.

Treatment continued, and he was seen again on October 26 for a progress evaluation, with the results as shown in table 2-4:

TABLE 2-4

|  | Right Eye | Left Eye |
|---|---|---|
| Snellen Chart | 20/30 plus 2 | 20/25 plus 2 |
| Contrast sensitivity | 20/25 | 20/25 |

The color field had continued to expand on visual field measurement. The blind spot was still enlarged in both eyes.

Treatment continued, and he was seen after approximately 30 treatments on November 20, with the results as seen in table 2-5.

TABLE 2-5

|  | Right Eye | Left Eye |
|---|---|---|
| Snellen Chart | 20/30 plus 3 | 20/25 plus 2 |
| Contrast sensitivity | 20/30 | 20/25 |

The visual field was repeated, and the color field had not expanded to what would be considered normal levels. The blind spot was only enlarged by about 10% now in each eye.

Treatments continued through December 16, with all findings remaining the same. In a progress evaluation on February 12 of the following year, the results were as shown in table 2-6.

TABLE 2-6

|  | Right Eye | Left Eye |
| --- | --- | --- |
| Snellen Chart | 20/30 plus 1 | 20/25 plus 2 |
| Contrast sensitivity | 20/25 | 20/25 |

Subjectively, he reported much better vision both at far and near, could read easily, drive safely, and reported that he was seeing things much brighter and clearer at all distances, and at all times.

EXAMPLE 3

Patient HD was born on Apr. 2, 1919, and was first seen on June 6 with a history of macular degeneration, and central scotoma with metamorphosis. No other ocular pathology was noted, and the she was on no medication.

Measurement of her central visual field revealed a large central scotoma in each eye corresponding to the macular area. Her visual acuity is shown in table 3-1

TABLE 3-1

|  | Right Eye | Left Eye |
| --- | --- | --- |
| Snellen Chart | 20/100 | 20/70 |
| Contrast sensitivity | 20/100 | 20/80 |

Re-examination after her summer absence in the Fall revealed the results shown in table 3-2.

TABLE 3-2

|  | Right Eye | Left Eye |
| --- | --- | --- |
| Contrast sensitivity | 20/100–20/200 | 20/70 |

She began a series of transocular electrical conduction treatments under the conditions of Example 1, except that the treatments were performed weekly for six weeks.

Re-examination on November 11 revealed the results shown in table 3-3.

TABLE 3-3

|  | Right Eye | Left Eye | Both eyes |
| --- | --- | --- | --- |
| Snellen Chart | 20/50 plus 2 | 20/40 plus 2 | 20/30 |
| Contrast sensitivity | 20/100 | 20/50 |  |

She reported that an ophthalmologist who saw her the previous week said that her visual acuity was now stable, and that ocular hemorrhage had diminished. She reported seeing much better at all distances and was able to read comfortably and efficiently.

EXAMPLE 4

Patient CR was born Feb. 13, 1917, and was first seen on December 9. A cataract had been removed from the right eye, and she at that time had a cataract in the left eye. She had a diagnosis of senile macular degeneration in both eyes. She was taking medication for hypertension, iron for anemia, and occasionally a sleeping pill.

Her best corrected acuity was OD 4/200th's vision, OS 10/70th's vision, near acuity was 1.2M. Due to her poor vision, contrast sensitivity testing was not possible. By placing a 2.5 power telescope in front of the left eye, visual acuity could be improved to 20/40 minus 1.

Transocular electrical conduction treatment was begun under the conditions of Example 1. After seven treatments her visual acuity was OD 400; OS 20/80 plus 1. Her near visual acuity was now 1M with reading glasses. A 2.5 power telescope in front of the left eye produced a visual acuity of 20/40 plus 2. She reported much improved subjective visual acuity both at far and near, and noticed that vitreous floaters had improved.

After six more treatments she was re-evaluated on February 17 of the next year. Visual acuity was OD 20/400; OS 20/70. Visual acuity through a 2.5 power telescope was almost 20/30.

In summary her acuity in each eye improved approximately 100% over a course of 13 sessions.

EXAMPLE 6

Patient HD from Example 3 was subsequently treated weekly over a period of 12 weeks with pulsed electrical current using the Liss Cranial Stimulator noted herein. The stimulator was operated at 400 microamperes for 10 minutes. The wave form consisted of "on:" periods of pulse trains alternating with "off periods" at 500 hz and a duty cycle of 3:1. The pulse trains occurred at a frequency of 15 khz and were amplitude modulated at 15 hz. Results were as follows:

TABLE 6-1

|  | Right Eye | Left Eye |
| --- | --- | --- |
| Before Treatment | 20/50-1 | 20/50-2 |
| After Treatment | 20/40-1 | 20/40-2 |

EXAMPLE 7

Patient CT complained of bilateral vitreous floaters, and underwent transocular electrical conduction treatment was performed according to the conditions of Example 1, except that treatments were undertaken thrice weekly for a period of two weeks. After completion of the treatments the patient reported that the floaters were no longer perceptible.

While this invention has been explained with reference to the structure disclosed herein, it is not confined to the details set forth and this application is intended to cover any modifications and changes as may come within the scope of the following claims:

What is claimed is:

1. A nondestructive method of treating ocular pathology in a human subject, comprising the steps of:

placing a first electrode of a direct current source in direct electrical contact with an eyelid of a subject wherein said first electrode is in a proximity with said eye thereof;

placing a second electrode of said source in direct electrical contact with a skin site on the subject that is remote from the eye thereof; and causing a low level direct electrical current to flow between said electrodes through the subject at between 5 and 1000 µA for a period of time insufficient to harm living eye tissue to restore cellular electrical balance within the eye.

2. The method in accordance with claim 1, wherein said source is a portable direct current generator, and further comprising the step of maintaining said current at about 200 µA.

3. The method in accordance with claim 1, wherein said step of placing a first electrode of a direct current source in electrical contact with a subject in a proximity of an eye thereof comprises placing a positive electrode in electrical contact with a subject in a proximity of an eye thereof; and said step of placing a second electrode of said source in electrical contact with a site on the subject that is remote from the eye thereof comprises placing a negative electrode in electrical contact with a site on the subject that is remote from the eye thereof.

4. The method in accordance with claim 1, wherein said step of placing a second electrode of said source in electrical contact with a site on the subject that is remote from the eye thereof comprises placing a second electrode on the posterior neck of the subject.

5. The method in accordance with claim 1, further comprising the step of maintaining the current flow for about 10 minutes.

6. A nondestructive method of treating macular degeneration in a subject, comprising the steps of:

placing a first electrode of a current source in indirect electrical communication with an eye of a subject;

placing a second electrode of said source in electrical contact with a site on the subject that is remote from the eye thereof;

causing a low level electrical current of between 5 and 1000 µA to flow between said electrodes through the subject for a period of time insufficient to harm living eye tissue; and repeating the last mentioned step a sufficient number of times to improve the subject's visual activity.

7. The method according to claim 6, wherein said source is a portable direct current generator, further comprising the step of maintaining said electrical current at a constant magnitude of about 200 µA.

8. The method according to claim 6, wherein said step of placing a first electrode of a direct current source in electrical contact with a subject in proximity to an eye thereof comprises placing a positive electrode in electrical contact with an eye; and said step of placing a second electrode of said source in electrical contact with a site on the subject that is remote from the eye thereof comprises placing a negative electrode in electrical contact with a site on the subject that is remote from the eye thereof.

9. The method according to claim 6, wherein said step of placing a second electrode of said source in electrical contact with a site on the subject that is remote from the eye thereof comprises placing a second electrode on the posterior neck of the subject.

10. A method of treating macular degeneration in a subject, comprising the steps of:

placing a first electrode of a direct current generator on a subject in a proximity of an eye thereof;

placing a second electrode of said source in electrical contact with a site on the subject that is remote from the eye thereof; causing a nondestructive direct electrical current of between 5 and 1000 µA to flow between said electrodes through the subject; and affixing said generator to the subject for ambulation therewith; whereby the subject is enabled to ambulate while the direct current is flowing therethrough.

11. The method according to claim 10, wherein said generator is battery powered.

12. A non destructive method of treating hypertension in a subject, comprising the steps of:

placing a first electrode of a current source in indirect electrical communication with an eye of a subject;

placing a second electrode of said source in electrical contact with a site that is remote from the eyelid of the subject;

causing a low level electrical current between 5 and 1000 µA to flow between said electrodes through the subject for a period of time insufficient to harm living eye tissue; and repeating the last mentioned step a sufficient number of times to relieve hypertension.

13. The method according to claim 12, wherein said source is a portable direct current generator, further comprising the step of maintaining said electrical current at a constant magnitude of about 200 µA.

14. The method according to claim 12, wherein said step of placing a first electrode of a direct current source in electrical contact with a subject in proximity of an eye thereof comprises placing a positive electrode in electrical contact with an eye; and said step of placing a second electrode of said source in electrical contact with a site on the subject that is remote from the eye thereof comprises placing a negative electrode in electrical contact with a site on the subject.

15. The method according to claim 12, wherein said step of placing a second electrode of said source in electrical contact with a site on the subject that is remote from the eye thereof comprises placing a second electrode on the posterior neck of the subject.

16. A method of treating hypertension in a subject, comprising the steps of:

placing a first electrode of a direct current generator on a subject in a proximity of an eye thereof;

placing a second electrode of said source in electrical contact with a site that is remote from the eyelid of the subject;

causing a nondestructive direct electrical current between 5 and 1000 µA to flow between said electrodes through the subject for about 10 minutes; and affixing said generator to the subject for ambulation therewith;

whereby the subject is enabled to ambulate while receiving treatment.

17. The method according to claim 16, wherein said generator is battery powered.

18. A nondestructive method of treating vitreous ocular floaters, comprising the steps of:

placing a first electrode of a current source in indirect electrical communication with an eye a subject;

placing a second electrode of said source in electrical contact with a site on the subject that is remote from the eye thereof;

causing a low level electrical current of between 5 and 1000 µA to flow between said electrodes through the subject for a period of time insufficient to harm living eye tissue; and repeating the last mentioned step a sufficient number of times to eliminate ocular floaters.

19. The method according to claim 18, wherein said source is a portable direct current generator, further comprising the step of maintaining said electrical current at a constant magnitude of about 200 µA.

20. The method according to claim 18, wherein said step of placing a first electrode of a direct current source in electrical contact with a subject in a proximity of an eye thereof comprises placing a positive electrode in electrical contact with an eye thereof; and said step of placing a second electrode of said source in electrical contact with a site on the subject that is remote from the eye thereof comprises placing a negative electrode in electrical contact with a site on the subject that is remote from the eye thereof.

21. The method according to claim 18, wherein said step of placing a second electrode of said source in electrical contact with a site on the subject that is remote from the eye thereof comprises placing a second electrode on the posterior neck of the subject.

22. A method of treating vitreous ocular floaters, comprising the steps of:

placing a first electrode of a direct current generator on a subject in a proximity of an eye thereof;

placing a second electrode of said source in electrical contact with a site on the subject that is remote from the eye thereof;

causing a nondestructive direct electrical current of between 5 and 1000 µA to flow between said electrodes through the subject; and affixing said generator to the subject for ambulation therewith;

whereby the subject is enabled to ambulate while the direct current is flowing therethrough.

23. The method according to claim 22, wherein said generator is battery powered.

* * * * *